(12) United States Patent
Venancio (10) Patent No.: US 8,792,994 B2
(45) Date of Patent: Jul. 29, 2014

(54) TORSED SLEEVE LEAD ANCHOR AND SYSTEMS AND METHODS OF MANUFACTURE AND USE THEREOF

(71) Applicant: Boston Scientific Neuromodulation Corporation, Valencia, CA (US)

(72) Inventor: Cameron Venancio, San Luis Obispo, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 14/101,675

(22) Filed: Dec. 10, 2013

(65) Prior Publication Data

US 2014/0172055 A1     Jun. 19, 2014

Related U.S. Application Data

(60) Provisional application No. 61/739,371, filed on Dec. 19, 2012.

(51) Int. Cl.
*A61N 1/00* (2006.01)
*A61N 1/05* (2006.01)

(52) U.S. Cl.
CPC ..................... *A61N 1/05* (2013.01)
USPC ........................................... 607/116

(58) Field of Classification Search
USPC ........................................... 607/116
See application file for complete search history.

(56) References Cited

U.S. PATENT DOCUMENTS

| | | | |
|---|---|---|---|
| 6,181,969 B1 | 1/2001 | Gord | |
| 6,473,654 B1 * | 10/2002 | Chinn | 607/126 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2007/0150036 A1 | 6/2007 | Anderson | |
| 2011/0224764 A1 * | 9/2011 | Kulle | 607/116 |

* cited by examiner

*Primary Examiner* — Robert N Wieland
(74) *Attorney, Agent, or Firm* — Lowe Graham Jones PLLC; Bruce E. Black (57) ABSTRACT

A lead anchor includes a first outer shell and a second outer shell adjacent the first outer shell. The first outer shell defines a first opening and the second outer shell defines a second opening, and the first and second outer shells together define a lead lumen extending from the first opening to the second opening. The lead anchor also includes a flexible sleeve disposed in the lead lumen and attached to both the first outer shell and the second outer shell. The first and second outer shells are configured and arranged to rotate relative to each other and cause the flexible sleeve to twist within the lead lumen to facilitate gripping of a lead within the lead lumen.

20 Claims, 8 Drawing Sheets

TORSED SLEEVE LEAD ANCHOR AND SYSTEMS AND METHODS OF MANUFACTURE AND USE THEREOF

CROSS-REFERENCE TO RELATED APPLICATIONS

This application claims the benefit under 35 U.S.C. §119(e) of U.S. Provisional Patent Application Ser. No. 61/739,371 filed Dec. 19, 2012, which is incorporated herein by reference.

FIELD

The present invention is directed to the area of implantable electrical stimulation systems and methods of making and using the systems. The present invention is also directed implantable torsed sleeve anchors for electrical stimulation leads, as well as methods of making and using the anchors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

A lead anchor can be used to hold an implanted lead in place within patient tissue. A variety of lead anchors are available, but many conventional lead anchors use metallic components, such as screws, and have relatively large profile which can increase patient discomfort or tissue damage.

BRIEF SUMMARY

One embodiment is a lead anchor including a first outer shell and a second outer shell adjacent the first outer shell. The first outer shell defines a first opening and the second outer shell defines a second opening, and the first and second outer shells together define a lead lumen extending from the first opening to the second opening. The lead anchor also includes a flexible sleeve disposed in the lead lumen and attached to both the first outer shell and the second outer shell. The first and second outer shells are configured and arranged to rotate relative to each other and cause the flexible sleeve to twist within the lead lumen to facilitate gripping of a lead within the lead lumen.

Another embodiment is an implantable stimulation device that includes a lead having a proximal portion and a distal portion and an electrode array disposed along the distal portion of the lead; and the lead anchor describe above and configured and arranged to slidably receive a portion of the lead. The implantable stimulation device may also include a control module, a lead extension, or both.

Yet another embodiment is a method of implanting an electrical stimulation lead that includes slidably disposing the lead anchor describe above onto a lead with a portion of the lead disposed in the lead lumen of the lead anchor; and rotating the second outer shell relative to the first outer shell causing the flexible sleeve to twist and grip the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable torsed sleeve anchors for electrical stimulation leads, as well as methods of making and using the anchors and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
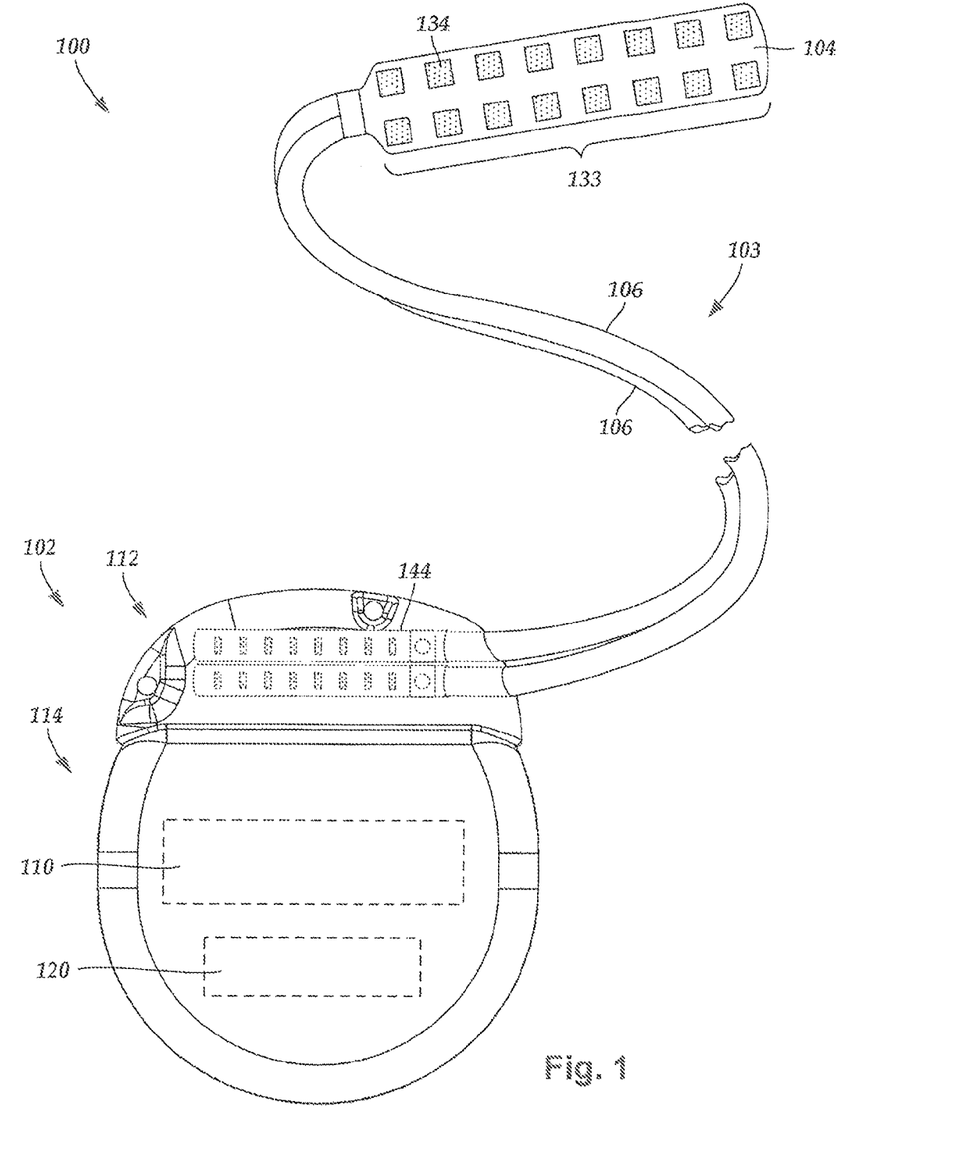
FIG. 1 is a schematic side view of one embodiment of an electrical stimulation system that includes a paddle lead electrically coupled to a control module, according to the invention.
Figure 2:
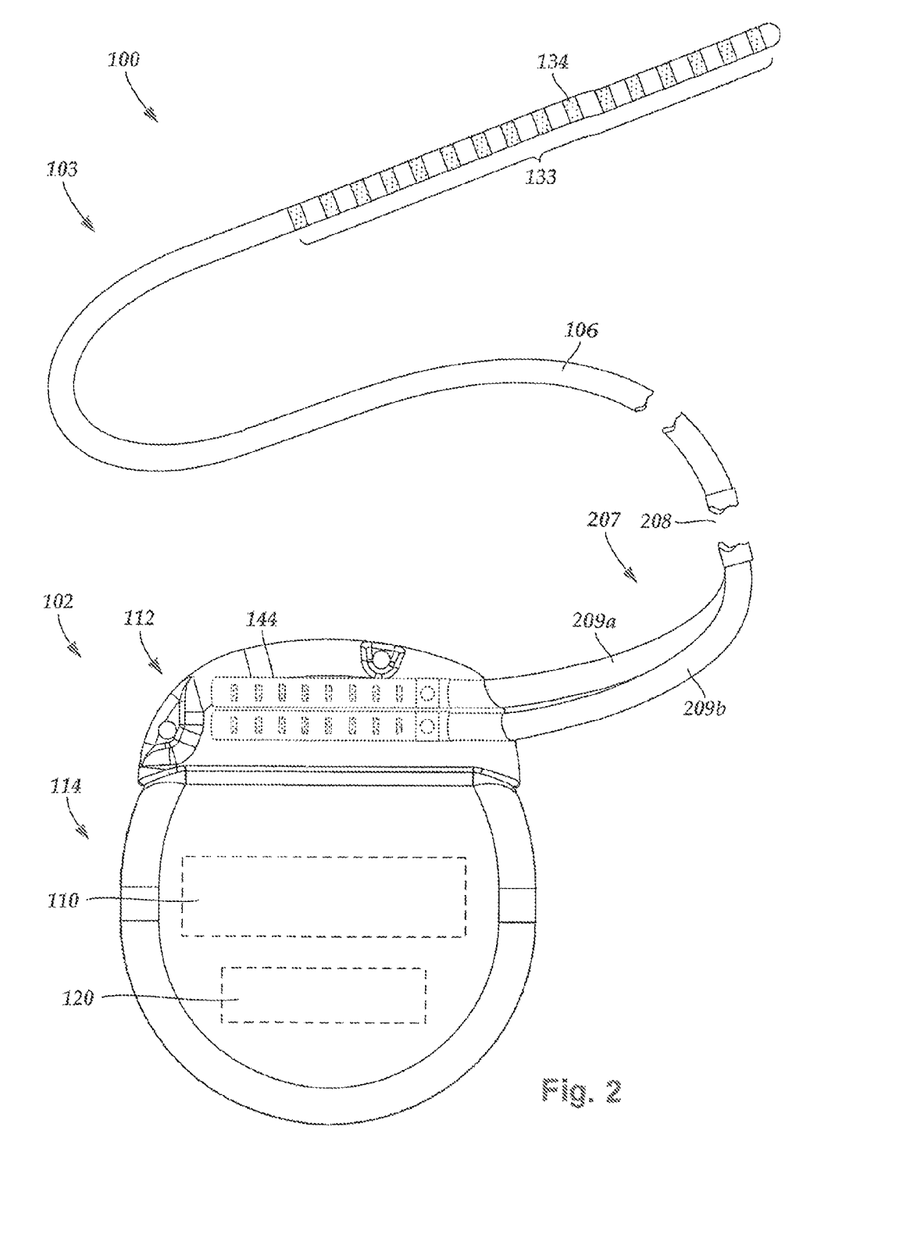
FIG. 2 is a schematic side view of one embodiment of an electrical stimulation system that includes a percutaneous lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
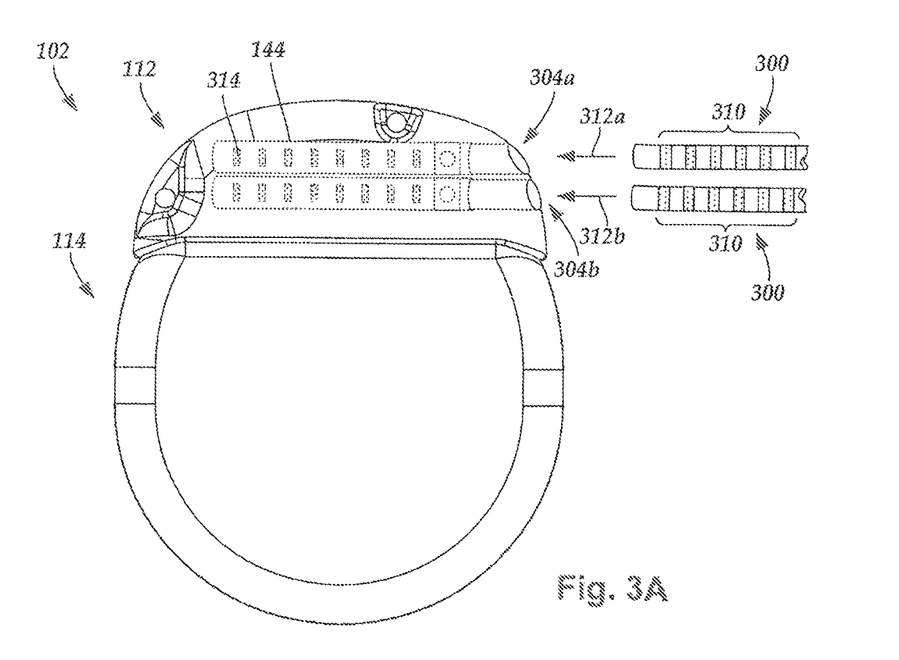
FIG. 3A is a schematic side view of one embodiment of the control module of FIG. 1 configured and arranged to electrically couple to an elongated device, according to the invention.
Figure 3B:
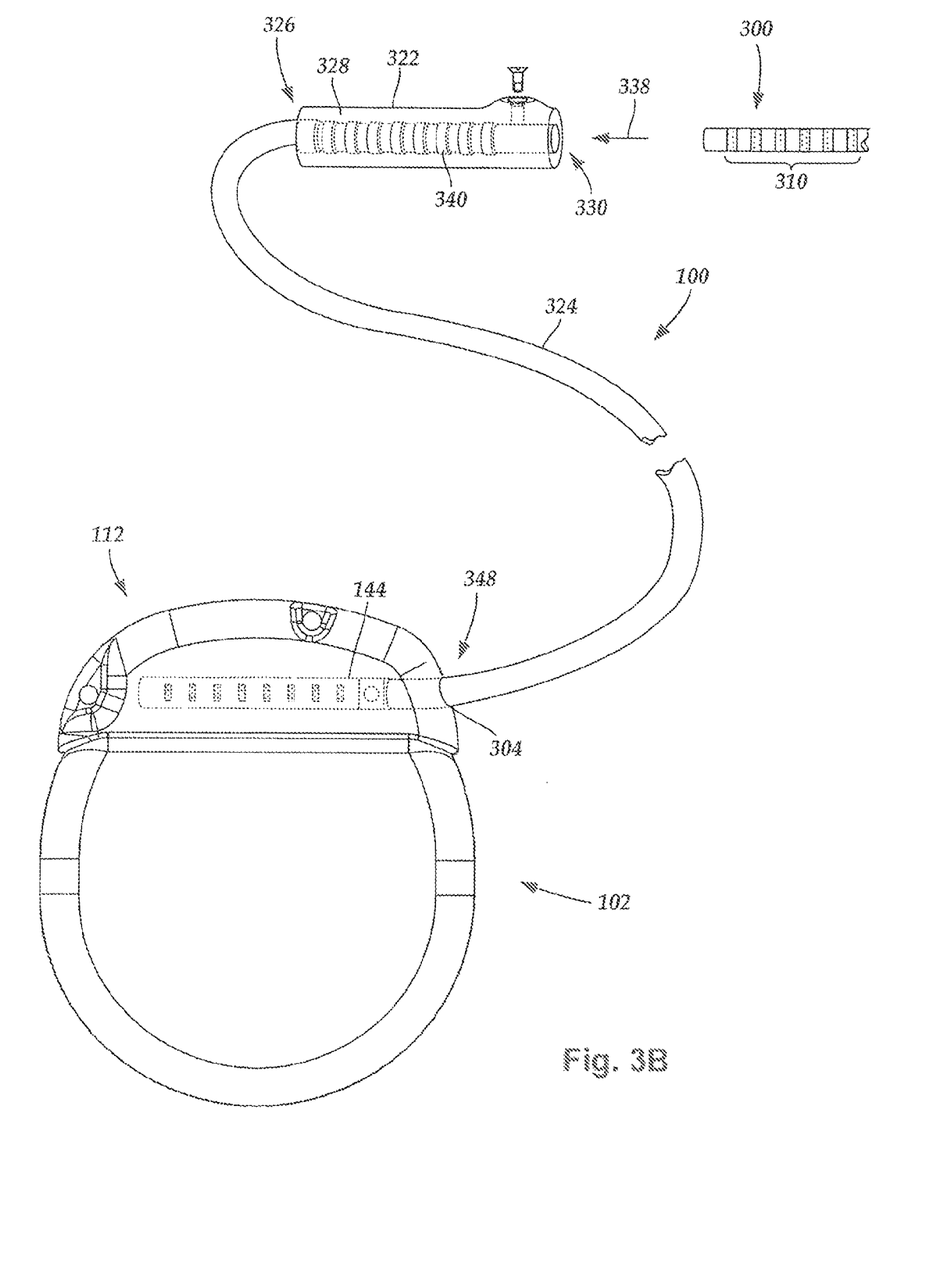
FIG. 3B is a schematic side view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead anchor can be used to anchor a lead or a lead extension to surrounding tissue. A torsed sleeve lead anchor includes a flexible sleeve disposed within an outer casing having two outer shells to which the flexible sleeve is attached. The outer shells can rotate with respect to each other to apply torsion (i.e., to torse) or otherwise twist the flexible sleeve to cause the flexible sleeve to grip a lead onto which the lead anchor is disposed. In at least some embodiments, torsing or otherwise twisting the flexible sleeve causes a portion of the flexible sleeve to collapse radially inward toward a lead, if present in the lead anchor.

Figure 4A:
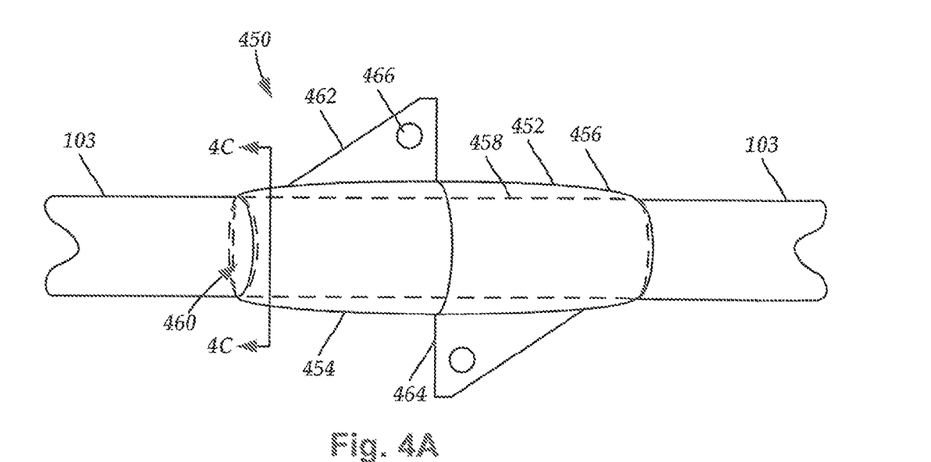
FIG. 4A is a schematic side view of one embodiment of a torsed sleeve lead anchor disposed on a portion of a sleeve and in a relaxed state, according to the invention.
Figure 4B:
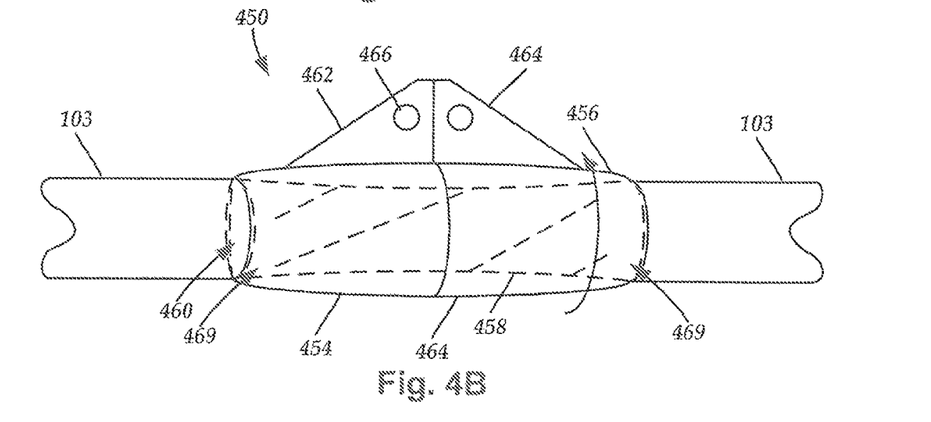
FIG. 4B is a schematic side view of the torsed sleeve lead anchor of FIG. 4A in a rotated state, according to the invention.
Figure 4C:
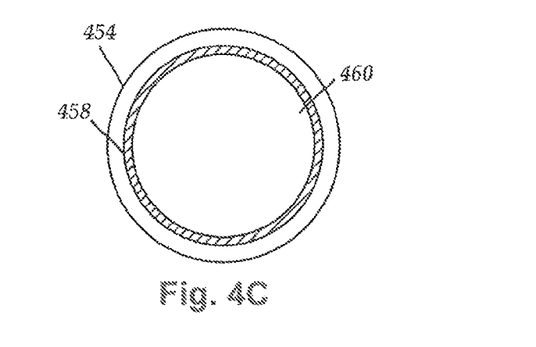
FIG. 4C is a schematic cross-sectional view of the torsed sleeve lead anchor of FIG. 4A, according to the invention.

FIGS. 4A-4C illustrate one embodiment of a torsed sleeve lead anchor 450 disposed on a lead 103. The lead anchor includes an outer casing 452 with a first outer shell 454 and a second outer shell 456 and a flexible sleeve 458 disposed within a lead lumen 460 of the outer casing. The flexible sleeve 458 is attached to both the first outer shell 454 and the second outer shell 456 so that when one (or both) of the two shells 454, 456 is rotated with respect to the other, the flexible sleeve is torsed or otherwise twisted. FIG. 4A illustrates the torsed sleeve lead anchor 450 in a relaxed position where the flexible sleeve 458 is not torsed or otherwise twisted. FIG. 4B illustrates torsed sleeve lead anchor 450 in a rotated position where the flexible sleeve 458 is torsed or otherwise twisted due to rotation of one or both of the shells 454, 456 relative to each other. It will be recognized that this lead anchor can be used with a lead extension, instead of a lead; and any reference to a lead in connection with the lead anchor is also applicable to a lead extension. It will also be recognized that more than one lead anchor can be attached to any lead or lead extension.

Each of the outer shells 454, 456 is more rigid that the flexible sleeve 458 and one or both of the outer shells can be rotated with respect to the other. This rigidity may be the result of, for example, material of the outer shells, thickness of the outer shells, or any other suitable characteristic or combination of characteristics The outer shells 454, 456 can be made of any suitable biocompatible material including, but not limited to, biocompatible metals and alloys, biocompatible plastics (particularly, rigid plastics), or composite materials.

In at least some embodiments, moving from the relaxed state to the rotated state includes rotating one or both of the outer shells relative to the other outer shell at least 60 degrees, 90 degrees, 120 degrees, 150 degrees, 180 degrees, or 185 degrees, or more. In at least some embodiments, moving from the relaxed state to the rotated state includes rotating one or both of the outer shells relative to the other outer shell by an amount in the range of 170 to 190 degrees, or in the range of 150 to 210 degrees.

Each of the outer shells 454, 456 has an opening through which the lead can pass. The outer shells 454, 456 define a lead lumen 460 within which a portion of the lead can reside. The lead lumen 460 extends between the openings in the outer shells. In at least some embodiments, when the lead anchor is in the relaxed state (for example, the state illustrated in FIG. 4A) the lead anchor is slidingly disposed on the lead allowing the lead anchor to slide over the lead to position the lead anchor at a desired place along the lead. In at least some embodiments, there may be sufficient friction between the lead anchor and the lead to retain the lead anchor in place on the lead until a practitioner slides the lead anchor over the lead. When the lead anchor is in the rotated position, however, the lead anchor grips the lead and resists sliding along the lead.

The flexible sleeve 458 is attached to each of the outer shells 454, 456. In at least some embodiments, the attachment region 469 is at or near the outer edge of each of the outer shells 454, 456 leaving the inner portion of the sleeve 458 unattached so that it can be torsed or otherwise twisted, as illustrated in FIG. 4B. In at least some embodiments, the flexible sleeve 458 is attached to the outer shells 454, 456 using an attachment region 469 that extends around the entire circumference of the lead lumen 460. In other embodiments, the attachment region 469 may only extend partially around the circumference of the lead lumen and, in some cases, may include one or more discrete, separated regions. The flexible sleeve 458 can be attached to the outer shells 454, 456 using any suitable attachment mechanism including, but not limited to, adhesive; mechanical attachment; fastener (e.g., a staple); melting, fusing, or reflowing the sleeve, the outer shell, or both to form the attachment; or the like.

In at least some embodiments, when the inner sleeve 458 is torsed or otherwise twisted, the middle section of the inner sleeve collapses radially inward to better grip a lead disposed within the lead anchor 450, as illustrated in FIG. 4B. The flexible sleeve 458 can be made of any suitable, flexible biocompatible material including, but not limited to, biocompatible plastics such as silicone, polyurethane, or combinations thereof. In at least some embodiments, the lead anchor does not contain any metallic components (e.g., any component that includes metal or an alloy).

The lead anchor 450 also includes a mechanism to lock the outer shells 454, 456 in place when in the rotated position. Any suitable locking mechanism can be used. As an example, the embodiment of the lead anchor 450 illustrated in FIGS. 4A to 4B includes locking elements 462, 464 on outer shells 454, 456, respectively. Optionally, one or more of the locking elements 462, 464 can include one or more suture apertures 466 through which a suture can pass to anchor the lead anchor 450 to surrounding tissue. Alternatively or additionally, one or more sutures may be wrapped around either, or both, of the outer shells 454, 456.

Figure 5A:
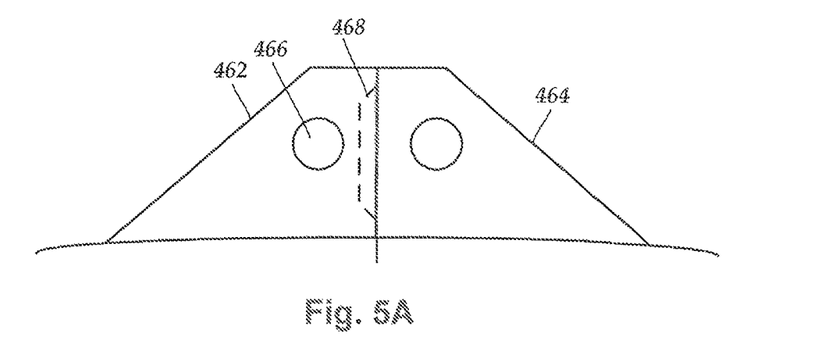
FIG. 5A is a schematic side view of a portion of torsed sleeve lead anchor with a first embodiment of a set of locking elements, according to the invention.
Figure 5B:
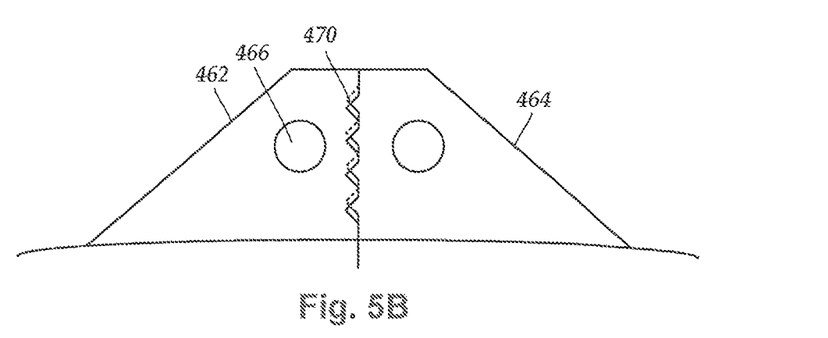
FIG. 5B is a schematic side view of a portion of torsed sleeve lead anchor with a second embodiment of a set of locking elements, according to the invention.
Figure 5C:
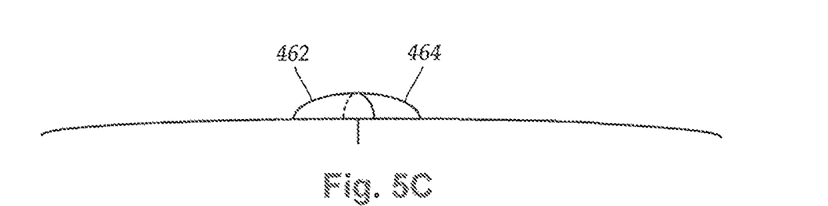
FIG. 5C is a schematic side view of a portion of torsed sleeve lead anchor with a third embodiment of a set of locking elements, according to the invention.

FIGS. 5A to 5C illustrate three different embodiments of the locking elements 462, 464. One or both of the locking element 462, 464 may include a tab, teeth, or some other portion of the locking element that will overlap with the other locking element and, when engaged, resist or prevent rotation of the outer shells 462, 464 back to the relaxed state.

The embodiment of FIG. 5A includes a first locking element 462 and a second locking element 464 with a tab 468 that fits behind the first locking element 462 when engaged in a locked position. The tab 468 when engaged resists or prevents rotation of the second locking element 462 back to the relaxed state of the outer shells 462, 464 (see FIG. 4A) and retains the outer shells 462, 464 in the rotated state (see FIG. 4B). During the initial rotation from the relaxed state to the rotated state, the practitioner pushes the tab 468 past the first locking element 462. The tab 468 then resists or prevents rotation back to the relaxed state. The size of the tab, the thickness of the tab, the material of the tab or locking element, or other characteristics of the tab, alone or in combination, may be selected to facilitate the resistance to rotation when the tab is engaged. It will be recognized that more than one tab may be used. It is also recognized that each of the locking elements 462, 464 may include one or more tabs.

The embodiment of FIG. 5B includes a first locking element 462 and a second locking element 464, each of which include one or more teeth 470 that are offset from each other so that the teeth 470 of the second locking element 464 fit behind, at least partially, the first locking element 462 when engaged in a locked position. The teeth 470 when engaged resists or prevents rotation of the second locking element 462 back to the relaxed state of the outer shells 454, 456 (see FIG. 4A) and retains the outer shells 454, 456 in the rotated state (see FIG. 4B). During the initial rotation from the relaxed state to the rotated state, the practitioner pushes the teeth 470 of the second locking element 464 past teeth 470 of the first locking element 462 or causes the 470 of the first and second locking elements to align so that they can pass by each other. The teeth 470 of the second locking element 464 then resist or prevent rotation back to the relaxed state. The size of the teeth, the thickness of the teeth, the number of the teeth, the arrangement of teeth, the material of the teeth or locking elements, or other characteristics of the teeth, alone or in combination, may be selected to facilitate the resistance to rotation when the teeth are engaged.

In some embodiments, the first locking element 462, tab 468, or teeth 470 (or any combination thereof) includes a beveled edge that facilitates transition of the tab 468 or teeth 470 past the first locking element 462 when rotating to the rotated position, but resists rotation back to the relaxed position.

FIG. 5C illustrates yet another embodiment where the first locking element 462 and the second locking element 464 are protrusions on the outer shells 454, 456. In at least some embodiments, one or both of the first and second locking elements 462, 464 have a beveled surface on one side to facilitate rotating the first and second locking elements past each other. The other side is not beveled in order to resist rotation back to the relaxed state.

Figure 6A:
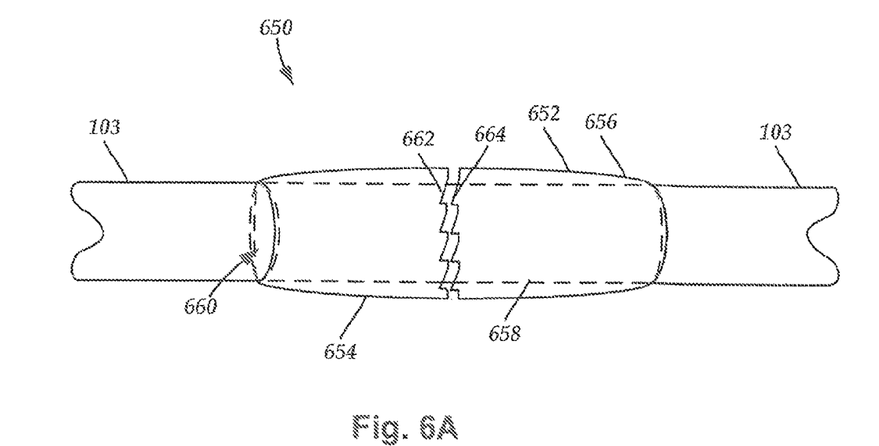
FIG. 6A is a schematic side view of a second embodiment of a torsed sleeve lead anchor disposed on a portion of a sleeve and in a relaxed state, according to the invention.
Figure 6B:
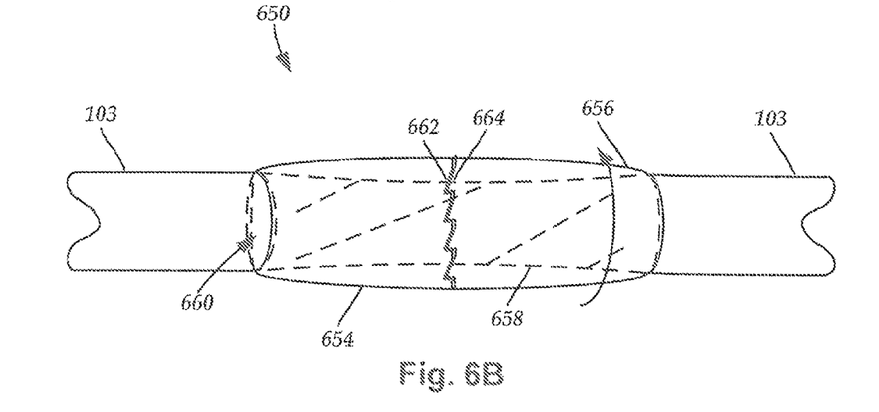
FIG. 6B is a schematic side view of the torsed sleeve lead anchor of FIG. 6A in a rotated state, according to the invention.

FIGS. 6A-6B illustrate another embodiment of a torsed sleeve lead anchor 650 disposed on a lead 103. The lead anchor includes an outer casing 652 with a first outer shell 654 and a second outer shell 656 and a flexible sleeve 658 disposed within a lead lumen 660 of the outer casing. The flexible sleeve 658 is attached to both the first outer shell 654 and the second outer shell 656 so that when one (or both) of the two shells 654, 656 is rotated with respect to the other, the flexible sleeve is torsed or otherwise twisted. FIG. 6A illustrates the torsed sleeve lead anchor 650 in a relaxed position where the flexible sleeve 658 is not torsed or otherwise twisted. FIG. 6B illustrates torsed sleeve lead anchor 650 in a rotated position where the flexible sleeve 658 is torsed or otherwise twisted due to rotation of one or both of the shells 654, 656 relative to each other. It will be recognized that this lead anchor can be used with a lead extension, instead of a lead; and any reference to a lead in connection with the lead anchor is also applicable to a lead extension. It will also be recognized that more than one lead anchor can be attached to any lead or lead extension. Optionally, one or both of the outer shells may include a fin or other element (not shown) extending from the outer shell and having a suture hole (not shown) to facilitate suturing of the lead anchor to surrounding tissue. Alternatively or additionally, one or more sutures may be wrapped around one or both of the outer shells and coupled to patient tissue.

The embodiment of the lead anchor illustrated in FIGS. 6A-6C is similar to the embodiment illustrated in FIGS. 4A-4C except that it utilizes a different locking mechanism. The lead anchor 650 illustrated in FIGS. 6A to 6B includes locking elements 662, 664 on adjacent surfaces of the outer shells 654, 656, respectively. In the illustrated embodiment, locking elements 662, 664 are teeth that do not engage in the relaxed position (FIG. 6A) and that lock (i.e., mate together) when the outer shells are rotated to the rotated position (FIG. 6B). It will be understood that engageable locking elements other than the illustrated teeth can be formed on the adjacent surfaces of the outer shells 654, 656. In at least some embodiments, the sleeve 658, or another element of the lead anchor 650, may further urge the two locking elements 662, 664 together when in the rotated position in order to maintain the engagement and mating of the locking elements 662, 664.

The size of the teeth, the thickness of the teeth, the number of the teeth, the arrangement of teeth, or other characteristics of the teeth, alone or in combination, may be selected to facilitate the resistance to rotation when the teeth are engaged. In some embodiments, the teeth of the first locking element 662 or the second locking element 664 (or both) include a beveled edge that facilitates transition of the teeth past the other locking element when rotating to the rotated position, but resists rotation back to the relaxed position. In at least some embodiments, a practitioner may disengage the two locking elements 662, 664 by pulling the two outer shells 654, 656 apart.

Figure 7:
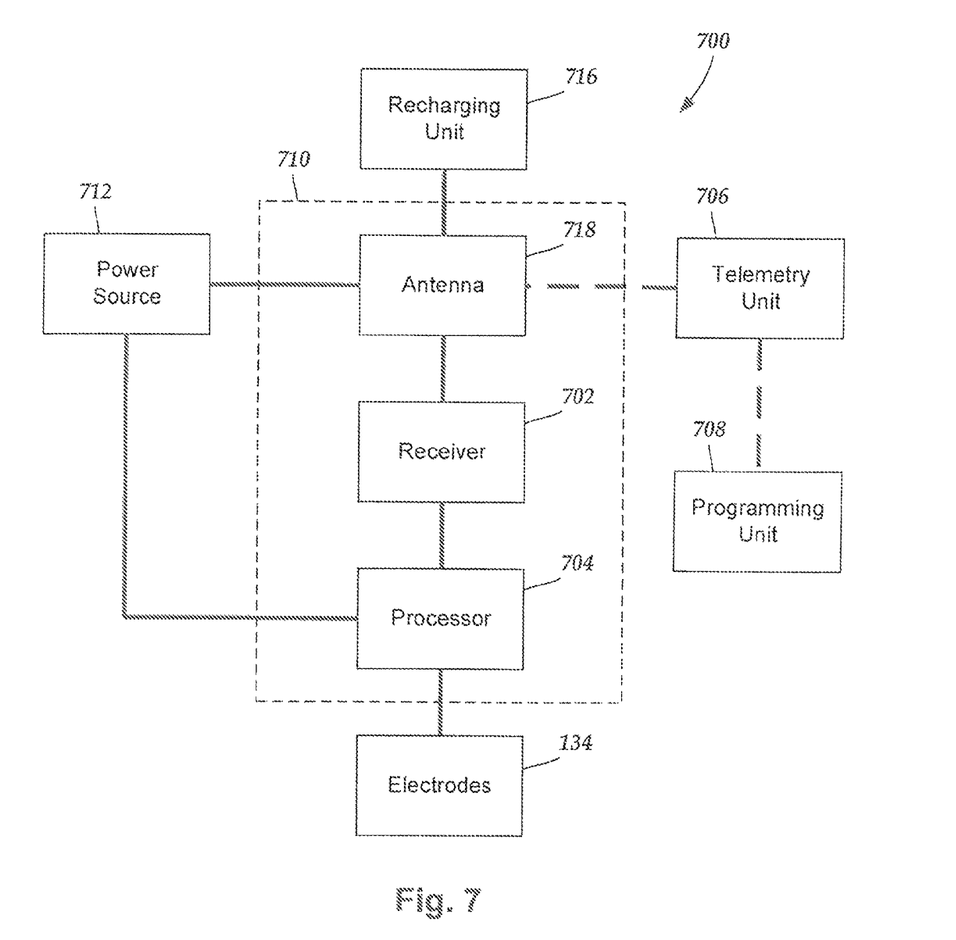
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
   a first outer shell;
   a second outer shell adjacent the first outer shell, wherein the first outer shell defines a first opening and the second outer shell defines a second opening, and the first and second outer shells together define a lead lumen extending from the first opening to the second opening; and
   a flexible sleeve disposed in the lead lumen and attached to both the first outer shell and the second outer shell, wherein the first and second outer shells are configured and arranged to be rotatable relative to each other and, when rotated, cause the flexible sleeve to twist within the lead lumen to facilitate gripping of a lead within the lead lumen.

2. The lead anchor of claim 1, wherein the first outer shell comprises a first locking element and the second outer shell comprises a second locking element and wherein the first and second locking elements are configured and arranged to engage when the second outer shell is rotated a predetermined amount relative the first outer shell to lock the first and second outer shells in a rotated state with the flexible sleeve twisted within the lead lumen.

3. The lead anchor of claim 2, wherein the first and second locking elements comprise teeth formed in opposing surfaces of the first and second outer shells, respectively.

4. The lead anchor of claim 2, wherein the second locking element comprises a tab that, in a locked position, is disposed behind the first locking element.

5. The lead anchor of claim 4, wherein the tab has a beveled edge to facilitate moving the tab past the first locking element when rotating the first and second outer shells relative to each other.

6. The lead anchor of claim 4, wherein the first locking element has a beveled edge to facilitate moving the tab past the first locking element when rotating the first and second outer shells relative to each other.

7. The lead anchor of claim 2, wherein the second locking element comprises a plurality of teeth that, in a locked position, are disposed at least partially behind the first locking element.

8. The lead anchor of claim 7, wherein the first locking element comprises a plurality of teeth.

9. The lead anchor of claim 1, wherein the flexible sleeve is attached to the first and second outer shells proximate to the first and second openings, respectively.

10. The lead anchor of claim 1, wherein the flexible sleeve is individually attached to each of the first and second outer shells around a circumferential attachment region of the inner lumen.

11. The lead anchor of claim 1, wherein the lead anchor has no metallic components.

12. The lead anchor of claim 1, wherein the lead anchor is configured and arranged to slidably receive the lead into the lead lumen when the lead anchor is in a relaxed state.

13. An implantable stimulation device, comprising:
    a lead having a proximal portion and a distal portion, the lead comprising an electrode array disposed along the distal portion of the lead; and
    the lead anchor of claim 1 configured and arranged to slidably receive a portion of the lead.

14. The implantable stimulation device of claim 13, further comprising a control module coupleable to the lead and configured and arranged to deliver stimulation current to the electrode array of the lead.

15. The implantable stimulation device of claim 13, wherein the lead anchor is disposed on the lead.

16. A method of implanting an electrical stimulation lead, the method comprising:
    slidably disposing the lead anchor of claim 1 onto a lead with a portion of the lead disposed in the lead lumen of the lead anchor; and
    rotating the second outer shell relative to the first outer shell causing the flexible sleeve to twist and grip the lead.

17. The method of claim 16, wherein rotating the second outer shell comprises rotating the second outer shell relative to the first outer shell causing the flexible sleeve to twist and collapse radially inward to grip the lead.

18. The method of claim 16, wherein the first outer shell comprises a first locking element and the second outer shell comprises a second locking element, wherein rotating the second outer shell comprises rotating the second outer shell to engage the second locking element with the first locking element so that the lead anchor remains in a rotated state.

19. The method of claim 18, wherein the second locking element comprises a tab and wherein rotating the second outer shell to engage the second locking element comprises rotating the tab past the first locking element on the first outer shell and then engaging the first locking element with the tab.

20. The method of claim 18, wherein the second locking element comprises a plurality of teeth and wherein rotating the second outer shell to engage the second locking element comprises rotating the teeth past the first locking element on the first outer shell and then engaging the first locking element with the teeth.

* * * * *